United States Patent

Hagmann et al.

[11] Patent Number: 5,919,776
[45] Date of Patent: Jul. 6, 1999

[54] SUBSTITUTED AMINOQUINOLINES AS MODULATORS OF CHEMOKINE RECEPTOR ACTIVITY

[75] Inventors: William K. Hagmann; Martin S. Springer, both of Westfield, N.J.

[73] Assignee: Merck & Co., Inc., Rahway, N.J.

[21] Appl. No.: 08/993,494

[22] Filed: Dec. 18, 1997

Related U.S. Application Data

[60] Provisional application No. 60/033,536, Dec. 20, 1996.
[51] Int. Cl.⁶ .................. A61K 31/47; A61K 31/475; A61K 31/49
[52] U.S. Cl. .................. 514/159; 514/160; 514/161; 514/162; 514/163; 514/167
[58] Field of Search .................. 514/159, 160, 514/161, 162, 163, 167

[56] References Cited

U.S. PATENT DOCUMENTS 5,441,963  8/1995  McDonald .................. 514/311
5,506,235  4/1996  Moyer .................. 514/296

OTHER PUBLICATIONS

Chemical Abstracts 116:51112, Lanza, 1992.
Medline 96210126, Legler, 1996.
Medline 94089760, Eaves, 1993.
Medline 94044787, Hori, 1993.
Chemical Abstracts 124:143381, Bennett, 1995.
Chemical Abstracts 124:199641, Toggas, 1996.

*Primary Examiner*—D. Margaret M. Mach
*Attorney, Agent, or Firm*—J. Eric Thies; David L. Rose

[57] ABSTRACT

The present invention is directed to aminoquinolines of Formula I:

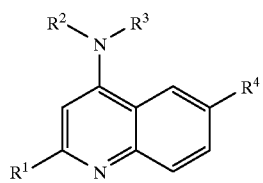

(wherein $R^1$, $R^2$, $R^3$, and $R^4$ are defined herein) which are useful as modulators of chemokine receptor activity. In particular, these compounds are useful as modulators of the chemokine receptors CCR-1, CCR-2, CCR-2A, CCR-2B, CCR-3, CCR-4, CCR-5, CXCR-3, and/or CXCR-4.

12 Claims, No Drawings

SUBSTITUTED AMINOQUINOLINES AS MODULATORS OF CHEMOKINE RECEPTOR ACTIVITY

CROSS REFERENCE TO RELATED APPLICATIONS

This application claims priority under 35 U.S.C. § 119(e) from U.S. Ser. No. 60/033,536, filed Dec. 20, 1996.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ($\alpha$) and C-C ($\beta$), depending on whether the first two cysteines are separated by a single amino acid (C-X-C) or are adjacent (C-C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al., *J. Biol. Chem.*, 270, 22123–22128 (1995); Beote, et al, *Cell*, 72, 415–425 (1993)); CCR2A and CCR-2B (or "CKR-2A"/"CKR-2A" or "CC-CKR-2A"/"CC-CKR2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270, 16491–16494 (1995); CCR-4 (or "CKR-4" or "CC-CKR-4") [MIP-1$\alpha$, RANTES, MCP-1] (Power, et al., *J. Biol. Chem.*, 270, 19495–19500 (1995)); CCR-5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation. Accordingly, agents which modulate chemokine receptors would be useful in such disorders and diseases.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 gyycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. Macrophage-tropic HIV and SIV envelope proteins have been shown to induce a signal through CCR-5 on CD4+ cells resulting in chemotaxis of T cells which may enhance the replication of the virus (Weissman, et al., *Nature*, 389, 981–985 (1997)). It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro apper to be unusually resistant to HIV-1 infection and are not immuno-compromised by the presence of this genetic variant (*Nature*, 382, 722–725 (1996)). Similarly, an alteration in the CCR-2 gene, CCR2-641, can prevent the onset of full-blown AIDS (Smith, et al., *Science*, 277, 959–965 (1997). Absence of CCR-5 appears to confer protection from HIV-1 infection (*Nature*, 382, 668–669 (1996)). An inherited mutation in the gene for CCR5, Delta 32, has been shown to abolish functional expression of the gene and individuals homozygous for the mutation are apparently not susceptible to HIV infection. Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). The $\beta$-chemokine macrophage-derived chemokine (MDC) has been shown to inhibit HIV-1 infection (Pal, et al., *Science*, 278 (5338), 695–698 (1997). The chemokines RANTES, MIP-1$\alpha$, MIP-1$\beta$, vMIP-I, vMIP-II, SDF-1 have also been shown to suppress HIV. A derivative of RANTES, (AOP)-RANTES, is a subnanomolar antagonist of CCR-5 function in monocytes (Simmons, et al., *Science,* 276, 276–279 (1997)). Monoclonal antibodies to CCR-5 have been reported to block infection of cells by HIV in vitro. Accordingly, an agent which could block chemokine receptors in humans who possess normal chemokine receptors should prevent infection in healthy individuals and slow or halt viral progression in infected patients (see *Science,* 275, 1261–1264 (1997)). By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β. Certain substituted aminoquinoline derivatives have been described as inhibitors of C5a receptor binding (Lanza, et al., *J. Med. Chem.,* 35, 252–258 (1992)).

SUMMARY OF THE INVENTION

The present invention is directed to compounds which are modulators of chemokine receptor activity and are useful in the prevention or treatment of certain inflammatory and immunoregulatory disorders and diseases, including asthma and allergic diseases, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

DETAILED DESCRIPTION OF THE INVENTION

The present invention is directed to compounds of Formula I:

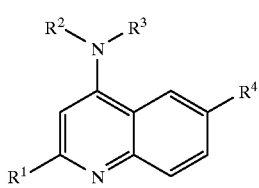

I wherein
$R^1$ is selected from:
(1) hydrogen,
(2) $C_{1-10}$alkyl, which is unsubstituted or substituted with one, two or three substituents each of which is independently selected from $R^5$,
(3) aryl, wherein aryl is selected from: phenyl and naphthyl which is unsubstituted or substituted with one, two or three substituents each of which is independently selected from $R^5$, (4) aryl$C_{1-10}$alkyl-, wherein aryl is defined above and alkyl is unsubstituted or substituted with one, two or three substituents each of which is independently selected from $R^5$,
(5) heteroaryl, wherein heteroaryl is selected from: benzimidazolyl, benzofuranyl, benzooxazolyl, furanyl, imidazolyl, indolyl, isooxazolyl, isoquinolinyl, isothiazolyl, oxadiazolyl, oxazolyl, pyrazinyl, pyrazolyl, pyridyl, pyrimidyl, pyrrolyl, quinolinyl, tetrazolyl, thiadiazolyl, thiazolyl, thienyl, triazolyl, which is unsubstituted or substituted with one, two or three substituents each of which is independently selected from $R^5$, and
(6) heteroaryl$C_{1-10}$alkyl-, wherein heteroaryl is defined above and alkyl is unsubstituted or substituted with one, two or three substituents each of which is independently selected from $R^5$;

$R^2$ and $R^3$ are independently selected from:
(1) hydrogen,
(2) $C_{1-10}$alkyl, which is unsubstituted or substituted with one, two or three substituents each of which is independently selected from $R^5$,
(3) aryl, wherein aryl is defined above,
(4) aryl$C_{1-10}$alkyl-, wherein aryl is defined above and alkyl is unsubstituted or substituted with one, two or three substituents each of which is independently selected from $R^5$, or $R^2$ and R3 together with the nitrogen to which they are attached form a heterocyclic ring of 5 to 7 members, such as: pyrrolidine, piperidine, piperazine, morpholine and thiomorpholine, wherein the heterocyclic ring optionally contains an additional group selected from —O—, —S—, and —NR$^6$—, and wherein the heterocyclic ring is unsubstituted or substituted with one, two or three substituents each of which is independently selected from $R^5$;

$R^4$ is selected from:
(1) —NH—C(=O)—X—R$^7$,
(2) —C(=O)—NH—R$^7$,
(3) —NH—C(=O)—(CH$_2$)$_n$—C(=O)—NH—R$^7$,
(4) —NH—S(=O)$_2$—X—R$^7$, and
(5) —NR$^8$R$^9$, wherein R$^8$ and R$^9$ are independently selected from:
(a) hydrogen,
(b) phenyl, and
(c) $C_{1-10}$alkyl;

$R^5$ is selected from:
(1) —O—R$^8$,
(2) —NO$_2$,
(3) halogen, wherein halogen is fluoro, chloro, bromo, or iodo,
(4) —S(=O)$_2$—R$^8$,
(5) —S—R$^8$,
(6) —S(=O)$_2$—NR$^8$R$^9$,
(7) —C$_{1-10}$alkyl,
(8) —NR$^8$R$^9$,
(9) —C(=O)—OR$^8$,
(10) —X—C(=O)—R$^8$,
(11) —CN,
(12) —C(=O)—NR$^8$R$^9$,
(13) —X—C(=O)—R$^8$,
(14) —NR$^{10}$—C(=O)—NR$^8$R$^9$, wherein R$^{10}$ is selected from:
(a) hydrogen,
(b) phenyl, and
(c) $C_{1-10}$alkyl;
(15) —NR$^{10}$—S(=O)$_2$—R$^8$,

(16) —NR$^{10}$—C(=NR$^{11}$)—NR$^8$R$^9$, wherein R$^{11}$ is selected from:
(a) hydrogen,
(b) phenyl, and
(c) C$_{1-10}$alkyl;
(17) —C(=NR$^{10}$)—NR$^8$R$^9$, and
(18) —CF$_3$;
R$^6$ is selected from:
(1) hydrogen,
(2) C$_{1-10}$alkyl, which is unsubstituted or substituted with one, two or three substituents each of which is independently selected from R$^5$,
(3) aryl, wherein aryl is defined above,
(4) arylC$_{1-10}$alkyl-, wherein aryl is as defined above and alkyl is unsubstituted or substituted with one, two or three substituents each of which is independently selected from R$^5$,
(5) —C(=O)—X—C$_{1-10}$alkyl, wherein alkyl is unsubstituted or substituted with one, two or three substituents each of which is independently selected from R$^5$,
(6) —S(=O)$_2$—X—C$_{1-10}$alkyl, wherein alkyl is unsubstituted or substituted with one, two or three substituents each of which is independently selected from R$^5$,
(7) —C(=O)—X-aryl, wherein aryl is defined above, and
(8) —S(=O)$_2$—X-aryl, wherein aryl is defined above;
R$_7$ is selected from:
(1) hydrogen,
(2) C$_{1-10}$alkyl, which is unsubstituted or substituted with one, two or three substituents each of which is independently selected from R$^5$,
(3) aryl, wherein aryl is defined above,
(4) arylC$_{1-10}$alkyl-, wherein aryl is defined above and alkyl is unsubstituted or substituted with one, two or three substituents each of which is independently selected from R$^5$,
(5) arylC$_{2-10}$alkenyl-, wherein aryl is defined above and alkenyl is unsubstituted or substituted with one, two or three substituents each of which is independently selected from R$^5$,
(6) heteroaryl, wherein heteroaryl is defined above, and
(7) heteroarylC$_{1-10}$alkyl-, wherein heteroaryl is defined above and alkyl is unsubstituted or substituted with one, two or three substituents each of which is independently selected from R$^5$, and
(8) heteroarylC$_{2-10}$alkenyl-, wherein heteroaryl is defined above and alkenyl is unsubstituted or substituted with one, two or three substituents each of which is independently selected from R$^5$;
X is selected from:
(1) a single bond,
(2) —O—, and
(3) —NR$^8$—;
n is an integer selected from 0 to 8;
and pharmaceutically acceptable salts thereof.

Preferred compounds for use in the present invention include those of Formula I wherein:
R$^1$ is unsubstituted C$_{1-10}$alkyl;
R$^2$ is hydrogen;
R$^3$ is selected from:
(1) hydrogen,
(2) —CH$_2$-phenyl, and
(3) unsubstituted C$_{1-10}$alkyl;
R$^4$ is selected from:
(1) —NH—C(=O)-phenyl,
(2) —NH—C(=O)-naphthyl,
(3) —NH—C(=O)-(unsubstituted C$_{1-10}$alkyl)-phenyl, wherein the phenyl is unsubstituted or substituted with one or two substituents selected from: fluoro, chloro, and trifluoromethyl,
(4) —NH—C(=O)-(unsubstituted C$_{1-10}$alkyl),
(5) —C(=O)—NH-(unsubstituted C$_{1-10}$alkyl), and
(6) —C(=O)—NH—CH$_2$-phenyl;
and pharmaceutically acceptable salts thereof.

Illustrating the present invention is the use of the compounds wherein heteroaryl is quinolinyl, substituted with —NH$_2$ and with —CH$_3$.

Preferred compounds for use in the present invention further include those of Formula Ia:

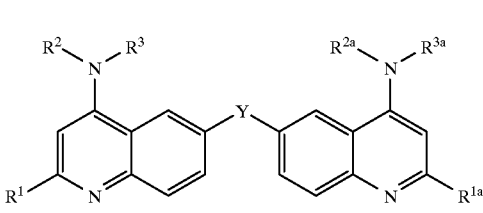

Ia wherein:
R$^1$ and R$^{1a}$ are independently selected from:
(1) hydrogen,
(2) C$_{1-10}$alkyl, which is unsubstituted or substituted with one, two or three substituents each of which is independently selected from R$^5$,
(3) aryl, wherein aryl is selected from: phenyl and naphthyl which is unsubstituted or substituted with one, two or three substituents each of which is independently selected from R$^5$, and
(4) arylC$_{1-10}$alkyl-, wherein aryl is defined above and alkyl is unsubstituted or substituted with one, two or three substituents each of which is independently selected from R$^5$;
R$^2$, R$^{2a}$, R$^3$ and R$^{3a}$ are independently selected from:
(1) hydrogen,
(2) C$_{1-10}$alkyl, which is unsubstituted or substituted with one, two or three substituents each of which is independently selected from R$^5$,
(3) aryl, wherein aryl is defined above,
(4) arylC$_{1-10}$alkyl-, wherein aryl is defined above and alkyl is unsubstituted or substituted with one, two or three substituents each of which is independently selected from R$^5$,
or R$^2$ and R$^3$ or R$^{2a}$ and R$^{3a}$ together with the nitrogen to which they are attached form a heterocyclic ring of 5 to 7 members, such as: pyrrolidine, piperidine, piperazine, morpholine and thiomorpholine, wherein the heterocyclic ring optionally contains an additional group selected from —O—, —S—, and —NR$^{6a}$, wherein R$^{6a}$ is independently selected from:
(a) hydrogen,
(b) phenyl, and
(c) C$_{1-10}$alkyl;
and wherein the heterocyclic ring is unsubstituted or substituted with one, two or three substituents each of which is independently selected from R$^5$;
Y is selected from:
(1) —NR$^8$—C(=O)—NR$^9$—, wherein R$^8$ and R$^9$ are independently selected from:
(a) hydrogen, (b) phenyl, and
(c) $C_{1-10}$alkyl;
(2) —$NR^8$—C(=O)—$(CH_2)_n$—C(=O)—$NR^9$—;
(3) —$NR^8$—S(=O)$_2$—$NR^9$—, and
(4) —C(=O)—NH—;

$R^5$ is selected from:
(1) —O—$R^8$,
(2) —$NO_2$,
(3) halogen, wherein halogen is fluoro, chloro, bromo, or iodo,
(4) —S(=O)$_2$—$R^8$,
(5) —S—$R^8$,
(6) —S(=O)$_2$—$NR^8R^9$,
(7) —$C_{1-10}$alkyl,
(8) —$NR^8R^9$,
(9) —C(=O)—$OR^8$,
(10) —X—C(=O)—$R^8$,
(11) —CN,
(12) —C(=O)—$NR^8R^9$,
(13) —X—C(=O)—$R^8$,
(14) —$NR^{10}$—C(=O)—$NR^8R^9$, wherein $R^{10}$ is selected from:
 (a) hydrogen,
 (b) phenyl, and
 (c) $C_{1-10}$alkyl;
(15) —$NR^{10}$—S(=O)$_2$—$R^8$,
(16) —$NR^{10}$—C(=$NR_2$)—$NR^8R^9$,
(17) —C(=$NR^{10}$)—$NR^8R^9$, and
(18) —$CF_3$;

n is an integer selected from 0 to 8;
and pharmaceutically acceptable salts thereof.

Preferred compounds for use in the present invention further include those of Formula Ia wherein:

$R^1$ and $R^{1a}$ are unsubstituted $C_{1-10}$alkyl;

$R^2$ and $R^{2a}$ are hydrogen;

$R^3$ and $R^{3a}$ are independently selected from:
(1) hydrogen,
(2) —$CH_2$-phenyl, and
(3) unsubstituted $C_{1-10}$alkyl;

Y is selected from:
(1) —NH—C(=O)—NH—,
(2) —NH—C(=O)—C(=O)—NH—,
(3) —NH—C(=O)—$CH_2$—C(=O)—NH—,
(4) —NH—C(=O)—$(CH_2)_4$—C(=O)—NH—,
(5) —NH—C(=O)—$(CH_2)_6$—C(=O)—NH—, and
(6) —NH—C(=O)—$(CH_2)_8$—C(=O)—NH—;
and pharmaceutically acceptable salts thereof.

Specific compounds of use in the present invention include:
(1) 4,6-Diamino-2-methyl-quinoline;
(2) 4-Amino-6-(2'-chloro-trans-cinnamoyl)amino-2-methyl-quinoline;
(3) 4-Amino-6-(trans-cinnamoyl)amino-2-methyl-quinoline;
(4) 4-Amino-6-(2-phenylethyl)amino-2-methyl-quinoline;
(5) 4-Amino-6-(2',6'-dichloro-trans-cinnamoyl)amino-2-methyl-quinoline;
(6) 4-Amino-6-(benzoyl)amino-2-methyl-quinoline;
(7) 4-Amino-6-(2'-naphthoyl)amino-2-methyl-quinoline;
(8) 4-Amino-6-(butanoyl)amino-2-methyl-quinoline;
(9) 4-Amino-6-(octanoyl)amino-2-methyl-quinoline;
(10) 4-Amino-6-(octadecanoyl)amino-2-methyl-quinoline;
(11) 4-Amino-6-(2'-trifluoromethyl-trans-cinnamoyl)amino-2-methyl-quinoline;
(12) 4-Amino-6-(3'-trifluoromethyl-trans-cinnamoyl)amino-2-methyl-quinoline;
(13) 4-Amino-6-(4'-trifluoromethyl-trans-cinnamoyl)amino-2-methyl-quinoline;
(14) 6-(2'-Chloro-trans-cinnamoyl)amino-4-methoxy-2-methyl-quinoline;
(15) 6-Amino-4-benzylamino-2-methyl-quinoline;
(16) 4-Benzylamino-6-(2'-chloro-trans-cinnamoyl)amino-2-methyl-quinoline;
(17) 4-Benzylamino-6-(2'-trifluoro-trans-cinnamoyl)amino-2-methyl-quinoline;
(18) 4-n-Octylamino-6-(2'-chloro-trans-cinnamoyl)amino-2-methyl-quinoline;
(19) 4-Amino-2-methyl-quinoline, N-n-octyl-6-carboxamide;
(20) 4-Amino-2-methyl-quinoline, N-benzyl-6-carboxamide;
(21) N,N'-Bis(4-amino-2-methyl-6-quinolyl)urea;
(22) N,N'-Bis(4-amino-2-methyl-6-quinolyl)oxalamide;
(23) N,N'-Bis(4-amino-2-methyl-6-quinolyl)malonamide;
(24) N,N'-Bis(4-amino-2-methyl-6-quinolyl)adipamide;
(25) N,N'-Bis(4-amino-2-methyl-6-quinolyl)sebacamide;
(26) N,N'-Bis(4-benzylamino-2-methyl-6-quinolyl)oxalamide;
(27) N,N'-Bis(2-methyl-6-quinolyl)urea;
and pharmaceutically acceptable salts thereof.

The subject compounds are useful in a method of modulating chemokine receptor activity in a patient in need of such modulation comprising the administration of an effective amount of the compound.

As appreciated by those of skill in the art, halogen as used herein are intended to include chloro, fluoro, bromo and iodo. The alkyl groups specified above are intended to include those alkyl groups of the designated length in either a straight or branched configuration. Similarly, C1–6, as in $C_{1-6}$alkyl is defined to identify the group as having 1, 2, 3, 4, 5, or 6 carbons. Exemplary of such alkyl groups are methyl, ethyl, propyl, isopropyl, butyl, sec-butyl, tertiary butyl, pentyl, isopentyl, hexyl, isohexyl, allyl, propargyl, and the like.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases. Exemplifying the invention is the use of the compounds disclosed in the Examples and elsewhere herein.

The present invention is directed to the use of the foregoing compounds as modulators of chemokine receptor activity. In particular, these compounds are useful as modulators of the chemokine receptors, including CCR-1, CCR-2, CCR-2A, CCR-2B, CCR-3, CCR-4, CCR-5, CXCR-3, and/or CXCR-4.

The present invention is further directed to the use of compounds of this general structure which are disclosed as being bacteriocidal, trypanocidal and antagonists of the C5a receptor. Such compounds are disclosed, for example, in: Lanza, et al., *J. Med. Chem.*, 35, 252–258 (1992); Jensch, et al. *Angew. Chem.*, 50, 891–902 (1937); Peng, et al. *J. Am. Chem. Soc.*, 78, 3703–3708 (1956); Pratt, M. G. and Archer, S. *J. Am. Chem. Soc.*, 70, 4065–4069 (1948); Schock, R. U. *J. Amer. Chem. Soc.*, 79, 1672–1675 (1957). Accordingly, the present invention embraces the use of a compound disclosed in these publications as a modulator of chemokine receptor activity.

The utility of the compounds in accordance with the present invention as modulators of chemokine receptor activity may be demonstrated by methodology known in the art, such as the assay for CCR-1 and/or CCR-5 binding as disclosed by Van Riper, et al., *J. Exp. Med.*, 177, 851–856 (1993), and the assay for CCR-2 and/or CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65(9), 4887–4892 (1991).

In particular, the compounds of the following examples had activity in binding to either the CCR-5 receptor or the CCR-3 receptor in the aforementioned assays. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, including asthma and allergic diseases, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases.

In another aspect, the instant invention may be used to evaluate putative specific agonists or antagonists of chemokine receptors, including CCR-1, CCR-2, CCR-2A, CCR-2B, CCR-3, CCR-4, CCR-5, CXCR-3, and CXCR-4. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-1, CCR-2, CCR-2A, CCR-2B, CCR-3, CCR-4, CCR-5, CXCR-3, and CXCR-4. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery. In addition, a compound of the present invention may be used for the prevention of infection by HIV and the prevention of AIDS, such as in post-coital prophylaxis or in the prevention of maternal transmission of the HIV virus to a fetus or a child upon birth.

In a preferred aspect of the present invention, a subject compound may be used in a method of inhibiting the binding of a human immunodeficiency virus to a chemokine receptor, such as CCR-5 and/or CXCR-4, of a target cell, which comprises contacting the target cell with an amount of the compound which is effective at inhibiting the binding of the virus to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as $\beta$2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| 141 W94 | Glaxo Wellcome | HIV infection, AIDS, ARC (protease inhibitor) |
| 1592U89 | Glaxo Wellcome | HIV infection, AIDS, ARC (protease inhibitor) |
| Abacavir (1592U89) | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/ Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| (−)6-Chloro-4(S)-cyclopropylethynyl-4(S)-trifluoromethyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-266 | DuPont-Merck Pharmaceuticals | HIV infection, AIDS, ARC (non-nucleoside reverse transcriptase inhibitor) |
| DMP-450 | AVID (Camden, NJ) | HIV infection, AIDS, ARC (protease inhibitor) |
| Efavirenz (DMP 266) | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse |

-continued

| Drug Name | Manufacturer | Indication |
|---|---|---|
| HBY097 | Hoechst Marion Roussel | transcriptase inhibitor) HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxythymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARG, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Megestrol Acetate | Bristol-Myers Squibb | treatment of anorexia assoc. w/AIDS |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples.

SCHEME 1

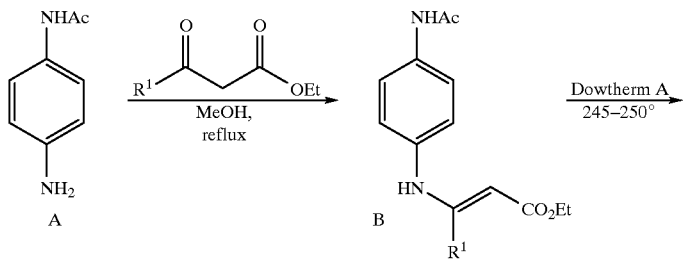

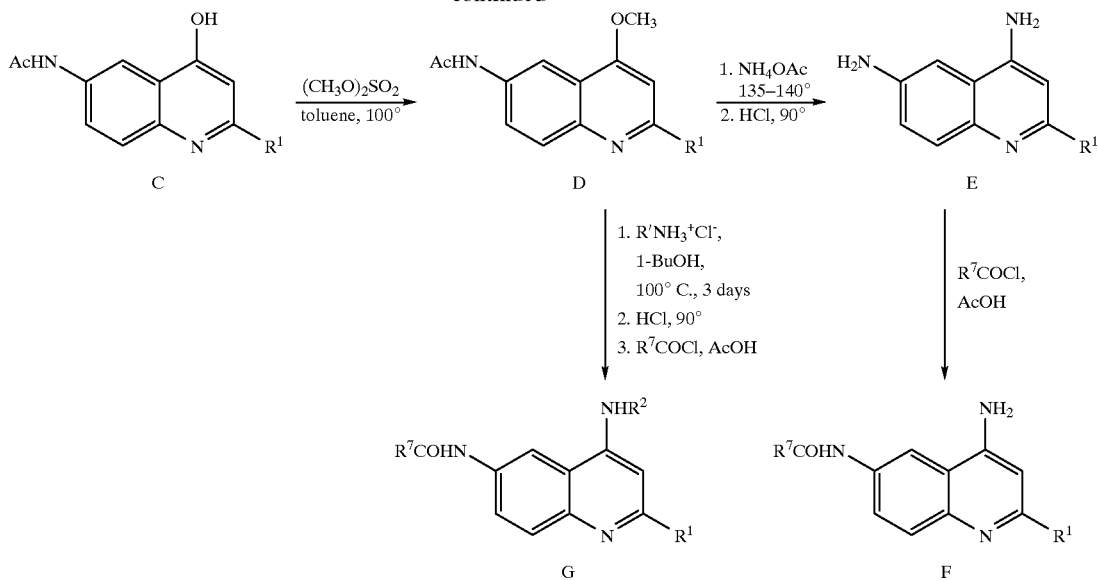

As shown in Scheme 1, the compounds of the present invention are prepared by procedures described for the preparation of N,N'-bis-(4-amino-2-methyl-6-quinolyl)urea and 6-N-(2-chloro-cinnamoyl)-4,6-diamino-2-methyl-quinoline according to literature procedures (see e.g., Jensch, et al. *Angew. Chem.*, 50, 891–902 (1937); Peng, et al. *J. Am. Chem. Soc.*, 78, 3703–3708 (1956)). 4-Acetamidoaniline A is condensed with an acyl acetate ester to form the enamine B. Heating of B yields 4-hydroxyquinoline C which is subsequently methylated with methyl sulfate to yield 4-methoxy-quinoline D. Heating of D with ammonium acetate followed by amide hydrolysis with hydrochloric acid gave 2-substituted 2,4-diaminoquinoline E. 2-Substituted 4,6-diamino-quinolines E were condensed with the appropriate acyl chlorides to give F. Displacement of the methyl ether in D with substituted amines followed by amide hydrolysis and reaction with acyl chlorides afforded compounds G.

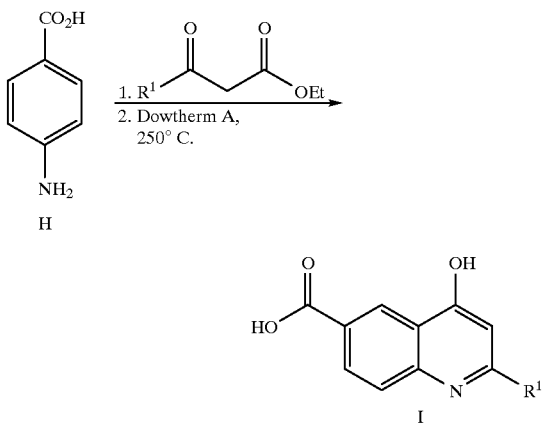

SCHEME 2

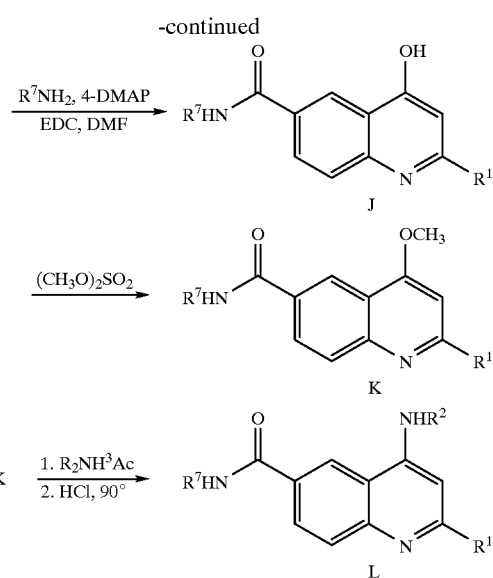

As shown in Scheme 2, the 6-inverso-amides of the present invention may be prepared by methods analogous to Scheme 1. p-Aminobenzoic acid H is condensed with an acyl acetate ester followed by thermolysis according to literature procedures (Schock, et al., *J. Am. Chem. Soc.*, 79, 1672–1675 (1957)) to give 2-substituted-4-hydroxy-quinoline-6-carboxylic acid I. Condensation of I with a substituted amine in the presence of carbodiimide and 4-dimethylaminopyridine gives amide J. Methylation with dimethyl sulfate gives methyl ether K which is subsequently displaced with an amine acetate to give amine L.

In some cases the order of carrying out the foregoing reaction schemes may be varied to facilitate the reaction or to avoid unwanted reaction products.

The following examples are provided for the purpose of further illustration only and are not intended to be limitations on the disclosed invention.

EXAMPLE 1

Bis-(4-Amino-2-methyl-quinolyl-6-oxalamide)

4,6-Diamino-2-methyl-quinoline (Pratt and Archer, *J. Am. Chem. Soc.*, 70, 4065–4069 (1948)) (1.0 g, 5.8 mmol) was placed in an oven-dried 100-mL three-necked flask under nitrogen followed by 6 mL of glacial acetic acid. Oxalyl chloride (0.25 mL, 2.89 mmol) was added dropwise to this solution over a 3 min period. A heavy precipitate formed, and the mixture was stirred for 1 h at room temperature. After addition of diethyl ether (25 mL), the solid was filtered, washed with ether and dried under vacuum. The hydrochloride salt was dissolved in 75 mL of warm water, the solution cooled to room temperature and made basic with 2.5N sodium hydroxide. The precipitated solid was filtered, washed with water, dried at 50° C. at high vacuum. Recrystallization was effected by dissolving the solid in warm DMF (30 mL), filtering, and adding diethyl ether to the point of turbidity. The crystals were collected by filtration, washed with ether, and dried under high vacuum; yield 0.52 g (45%); m.p. 243° (dec.).

The following additional compounds were prepared in an analogous fashion as Example 1, using malonyl chloride, adipoyl chloride, or sebacoyl chloride in place of oxalyl chloride, respectively:

N,N'-Bis(4-amino-2-methyl-6-quinolyl)malonamide, dihydrochloride (m.p. 255° C. dec).

N,N'-Bis(4-amino-2-methyl-6-quinolyl)adipamide, dihydrochloride (m.p. >300° C.).

N,N'-Bis(4-amino-2-methyl-6-quinolyl)sebacamide, dihydrochloride (m.p. 298° C. dec).

EXAMPLE 2

Bis-(4-Benzylamino-2-methyl-quinolyl-6-oxalamide)

A warm solution of benzylamine hydrochloride (1.5 g, 10.4 mmol) in water (2 mL) was added to a mixture of 6-acetamido-4methoxy-2-methylquinoline (2.0 g, 8.7 mmol) in n-butanol (20 mL). The mixture was stirred for 4 days at 100° C., cooled in an ice bath, and the resulting precipitated solid was filtered, washed with ether, and dried by suction to afford 2.1 g (71%) of 6-acetamido-4-benzylamino-2-methyl-quinoline hydrochloride. This material was heated in 25% hydrochloric acid (33 mL) for 5 h at 90° C. After cooling, the separated solid was filtered, washed with ether, and dried by suction. The solid was dissolved in water, made basic (pH >10) with 5N sodium hydroxide to afford a yellow solid that was filtered, washed with water, and dried. 6Amino-4-benzylamino-2-methyl-quinoline was obtained in 43% yield (0.98 g). 0.5 Grams (1.9 mmol) of this material was dissolved in glacial acetic acid, and the solution was treated with oxalyl chloride (0.17 mL) for 1 h at room temperature with stirring. Ether was then added (25 mL) and the mixture stirred for 30 min. The solid was filtered, washed with ether, and dried by suction. It was dissolved in water (25 mL) and warm ethanol (200 mL) with additional water added to achieve complete solution. After cooling to room temperature, 5N sodium hydroxide was added to give a yellow precipitate that was filtered, and dried under high vacuum to yield 0.46 g (41%) of the title compound; m.p. 292–294° (dec.); MS (FAB): m/z 581 (M+1).

EXAMPLE 3

4-Amino-6-(2'-trifluoromethyl-cinnamoyl)amino-2-methyl-quinoline 4,6-Diamino-2-methyl-quinoline (0.5 g, 2.9 mmol) was placed in an oven-dried 100-mL three-necked flask under nitrogen followed by 3 mL of glacial acetic acid. A solution of 2-(trifluoro-methyl)cinnamoyl chloride (0.68 g, 2.89 mmol) in 1 mL of glacial acetic acid was added dropwise over a 2 min period to this mixture. A heavy precipitate resulted. The mixture was stirred at room temperature for 1 hr, diethyl ether (25 mL) added, and the hydrochloride salt filtered, washed with ether, and dried at room temperature in vacuo. The hydrochloride salt was dissolved in a warm mixture of 50% aqueous methanol and the solution filtered. The solution was made basic with sodium bicarbonate solution and the resulting solid filtered, washed with water, and dried at 50° C. under high vacuum. Recrystallization from hot methanol gave 0.68 g (63%) of the desired product; m.p. 272–273°.

The following additional compounds were prepared in an analogous fashion as Example 3, using the appropriate acid chloride in place of 2-(trifluoromethyl)cinnamoyl chloride:

4-Amino-6-(2'-chloro-trans-cinnamoyl)amino-2-methyl-quinoline (m.p. 261–3° C.).

4-Amino-6-(trans-cinnamoyl)amino-2-methyl-quinoline (m.p. 255–6° C.).

4-Amino-6-(2-phenylethyl)amino-2-methyl-quinoline (m.p. 222–3° C.).

4-Amino-6-(2',6'-dichloro-trans-cinnamoyl)amino-2-methyl-quinoline (m.p. >300° C.).

4-Amino-6-(benzoyl)amino-2-methyl-quinoline (m.p. 246–7° C.).

4-Amino-6-(2'-naphthoyl)amino-2-methyl-quinoline (m.p. 270–1° C.).

4-Amino-6-(butanoyl)amino-2-methyl-quinoline (m.p. 242–3° C.).

4-Amino-6-(octanoyl)amino-2-methyl-quinoline (m.p. 227–9° C.).

4-Amino-6-(octadecanoyl)amino-2-methyl-quinoline (m.p. 134–5° C.).

4-Amino-6-(3'-trifluoromethyl-trans-cinnamoyl)amino-2-methyl-quinoline (m.p. 235–6° C.).

4-Amino-6-(4'-trifluoromethyl-trans-cinnamoyl)amino-2-methyl-quinoline (m.p. 267–9° C.).

EXAMPLE 4

6-(2'-Chlorocinnamoyl)amino-4-methoxy-2-methyl-quinoline

A solution of 2-chlorocinnamoyl chloride (prepared by treatment of 2-chlorocinnamic acid with oxalyl cloride and catalytic DMF in dichloromethane) (0.27 gm) in 1 mL acetic acid was added to a solution of 6-amino-4-methoxy-2-methyl-quinoline (0.25 g, 1.33 mmol) in glacial acetic acid (3 mL). A heavy precipitate formed, and the mixture was stirred for 1 h at room temperature. Ether (25 mL) was added and the solid was filtered, washed with ether, and dried by suction. The hydrochloride salt was suspended in warm water (25 mL) and ethanol (25 mL) and heated until dissolved. After cooling to room temperature, 5N sodium hydroxide was added to give a white precipitate that was filtered, and washed with water. Recrystallization from ethanol afforded the title compound; yield 0.27 g (58%); m.p. 228–229°; MS (FAB): m/z 353 (M+1).

EXAMPLE 5

4-Benzylamino-6-(2'-chlorocinnamoyl)amino-2-methyl-quinoline

A warm solution of benzylamine hydrochloride in water (1 mL) was added to a mixture of 6-acetamido-4-methoxy-2-methyl-quinoline (1.0 g, 4.3 mmol) in n-butanol (10 mL) after which complete solution occurred. The solution was stirred for 3 days at 100° C. under a nitrogen atmosphere, cooled, and the precipitated solid filtered, washed with ether, and dried to afford 1.0 g (75%) of 6-acetamido-4-benzylamino2-methyl-quinoline hydrochloride. A solution of this material (0.76 gm, 2.49 mmol) in 25% hydrochloric acid (12 mL) was heated for 5 hr at 90° C. and subsequently cooled. The precipitated solid was filtered, washed with water, dried at 50° C. under high vacuum for several hours to give 0.38 gm (58%) of 6-amino-4-benzylamino-2-methyl-quinoline. This material was dissolved in glacial acetic acid (3 mL) to which was added dropwise a solution of 2-chlorocinnamoyl chloride in glacial acetic acid over a 5 min period. The reaction mixture was stirred for 1 hr at room temperature and diluted with diethyl ether (25 mL). The solid was filtered, washed with ether, and dried by suction. It was then dissolved in a hot mixture of methanol (50 mL) and water (25 mL), cooled, and 5N sodium hydroxide added to give a yellow precipitate that was filtered, washed with water, and dried under high vacuum. Recrystallization from isopropanol afforded the title compound as pale yellow crystals; yield 0.32 g (52%), m.p. 253–4°, MS (FAB): m/z 428 (M+1).

The following additional compound was prepared in an analogous fashion as Example 5, n-octylamine hydrochloride in place of benzylamine hydrochloride in the first step of the sequence:

6-(2'-Chlorocinnamoyl)-4-(n-octylamino)-2-methyl-quinoline (m.p. 227–8° C.).

EXAMPLE 6

4-Amino-2-methyl-quinoline-6-carboxylic acid n-octyl amide

Step A: 4-Hydroxy-2-methyl-quinoline-6-carboxylic acid n-octyl amide

4-Dimethylaminopyridine (60 mg, 0.49 mmol), n-octylamine (1 mL, 6.1 mmol), and 1-(3-dimethylaminopropyl)-3-ethylcarbodiimide hydrochloride (1.1 g, 5.7 mmol) was added to a mixture of 4-hydroxy-2-methyl-quinoline-6-carboxylic acid$^{21}$ (1.0 g, 4.9 mmol) in N,N-dimethylformamide (20 mL). The reaction mixture was stirred overnight at room temperature, the solid filtered, washed with diethyl ether, and dried in vacuo; yield 1.4 g (90%); MS (FAB): m/z 315 (M+1).

Step B: 4-Methoxy-2-methyl-quinoline-6-carboxylic acid n-octyl amide

A mixture 4-hydroxy-2-methyl-quinoline-6-carboxylic acid n-octyl amide (1.3 g, 4.1 mmol) and dimethyl sulfate (0.7 mL, 7.4 mmol) in toluene (10 mL) was heated for 3 h at 100° C. with vigorous stirring. The toluene was decanted off and the remaining oil dissolved in water (15 mL) and treated with 1 mL 35% aqueous sodium hydroxide. The solid was filtered and washed with water. Purification was achieved by means of flash chromatography on silica gel using 4% methanol in dichloromethane as eluant. The product 23 was obtained as a crystalline solid; yield 0.91 g (67%); m.p. 143–145° C.; MS (FAB): m/z 329 (M+1).

Step C: 4-Amino-2-methyl-quinoline-6-carboxylic acid n-octyl amide

A mixture of 4-methoxy-2-methyl-quinoline-6-carboxylic acid n-octyl amide (0.75 g, 2.3 mmol) and ammonium acetate (2.5 g, 32.4 mmol) was heated for 3 h at 135° C., cooled, and then poured into water. The solid was filtered, washed with water, and dried by suction. It was then dissolved in 50% aqueous methanol, the solution made basic with 10% aqueous sodium hydrogencarbonate. The precipitated solid was filtered, washed with water, and dried in vacuo at 50° C.; yield 495 mg (69%); MS (FAB): m/z 314 (M+1).

The following additional compound was prepared in an analogous fashion as Example 6 using benzylamine in place of n-octylamine in the first step of the sequence:

4-Amino-2-methyl-quinoline, N-benzyl-6-carboxamide (MS (FAB): m/z 292 (M+1)).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for modulation of chemokine receptor activity in a mammal comprising the administration of an effective amount of a compound of formula I:

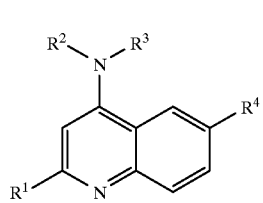

wherein $R^1$ is selected from:
(1) hydrogen,
(2) $C_{1-10}$alkyl, which is unsubstituted or substituted with one, two or three substituents each of which is independently selected from $R^5$,
(3) aryl, wherein aryl is selected from: phenyl and naphthyl which is unsubstituted or substituted with one, two or three substituents each of which is independently selected from $R^5$,
(4) aryl$C_{1-10}$alkyl-, wherein aryl is defined above and alkyl is unsubstituted or substituted with one, two or three substituents each of which is independently selected from $R^5$,
(5) heteroaryl, wherein heteroaryl is selected from: benzimidazolyl, benzofuranyl, benzooxazolyl, furanyl, imidazolyl, indolyl, isooxazolyl, isoquinolinyl, isothiazolyl, oxadiazolyl, oxazolyl, pyrazinyl, pyrazolyl, pyridyl, pyrimidyl, pyrrolyl, quinolinyl, tetrazolyl, thiadiazolyl, thiazolyl, thienyl, triazolyl, which is unsubstituted or substituted with one, two or three substituents each of which is independently selected from $R^5$, and
(6) heteroaryl$C_{1-10}$alkyl-, wherein heteroaryl is defined above and alkyl is unsubstituted or substituted with one, two or three substituents each of which is independently selected from $R^5$;

$R^2$ and $R^3$ are independently selected from:
(1) hydrogen,
(2) $C_{1-10}$alkyl, which is unsubstituted or substituted with one, two or three substituents each of which is independently selected from $R^5$,
(3) aryl, wherein aryl is defined above,
(4) aryl$C_{1-10}$alkyl-, wherein aryl is defined above and alkyl is unsubstituted or substituted with one, two or three substituents each of which is independently selected from $R^5$, or $R^2$ and $R^3$ together with the nitrogen to which they are attached form a heterocyclic ring of 5 to 7 members selected from pyrrolidine, piperidine, piperazine, morpholine and thiomorpholine, wherein the heterocyclic ring optionally contains an additional group selected from —O—, —S—, and —$NR^6$—, and wherein the heterocyclic ring is unsubstituted or substituted with one, two or three substituents each of which is independently selected from $R^5$;

$R^4$ is selected from:
(1) —NH—C(=O)—X—$R^7$,
(2) —C(=O)—NH—$R^7$,
(3) —NH—C(=O)—$(CH_2)_n$—C(=O)—NH—$R^7$,
(4) —NH—S(=O)$_2$—X—$R^7$, and
(5) —$NR^8R^9$, wherein $R^8$ and $R^9$ are independently selected from:
  (a) hydrogen,
  (b) phenyl, and
  (c) $C_{1-10}$alkyl;

$R^5$ is selected from:
(1) —O—$R^8$,
(2) —$NO_2$,
(3) halogen, wherein halogen is fluoro, chloro, bromo, or iodo,
(4) —S(=O)$_2$—$R^8$,
(5) —S—$R^8$,
(6) —S(=O)$_2$—$NR^8R^9$,
(7) —$C_{1-10}$alkyl,
(8) —$NR^8R^9$,
(9) —C(=O)—$OR^8$,
(10) —X—C(=O)—$R^8$,
(11) —CN,
(12) —C(=O)—$NR^8R^9$,
(13) —X—C(=O)—$R^8$,
(14) —$NR^{10}$—C(=O)—$NR^8R^9$, wherein $R^{10}$ is selected from:
  (a) hydrogen,
  (b) phenyl, and
  (c) $C_{1-10}$alkyl;
(15) —$NR^{10}$—S(=O)$_2$—$R^8$,
(16) —$NR^{10}$—C(=$NR^{11}$)—$NR^8R^9$, wherein $R^{11}$ is selected from:
  (a) hydrogen,
  (b) phenyl, and
  (c) $C_{1-10}$alkyl;
(17) —C(=$NR^{10}$)—$NR^8R^9$, and
(18) —$CF_3$;

$R^6$ is selected from:
(1) hydrogen,
(2) $C_{1-10}$alkyl, which is unsubstituted or substituted with one, two or three substituents each of which is independently selected from $R^5$,
(3) aryl, wherein aryl is defined above,
(4) aryl$C_{1-10}$alkyl-, wherein aryl is as defined above and alkyl is unsubstituted or substituted with one, two or three substituents each of which is independently selected from $R^5$,
(5) —C(=O)—X—$C_{1-10}$alkyl, wherein alkyl is unsubstituted or substituted with one, two or three substituents each of which is independently selected from $R^5$,
(6) —S(=O)$_2$—X—$C_{1-10}$alkyl, wherein alkyl is unsubstituted or substituted with one, two or three substituents each of which is independently selected from $R^5$,
(7) —C(=O)—X-aryl, wherein aryl is defined above, and
(8) —S(=O)$_2$—X-aryl, wherein aryl is defined above;

$R_7$ is selected from:
(1) hydrogen,
(2) $C_{1-10}$alkyl, which is unsubstituted or substituted with one, two or three substituents each of which is independently selected from $R^5$,
(3) aryl, wherein aryl is defined above,
(4) aryl$C_{1-10}$alkyl-, wherein aryl is defined above and alkyl is unsubstituted or substituted with one, two or three substituents each of which is independently selected from $R^5$,
(5) aryl$C_{2-10}$alkenyl-, wherein aryl is defined above and alkenyl is unsubstituted or substituted with one, two or three substituents each of which is independently selected from $R^5$,
(6) heteroaryl, wherein heteroaryl is defined above, and
(7) heteroaryl$C_{1-10}$alkyl-, wherein heteroaryl is defined above and alkyl is unsubstituted or substituted with one, two or three substituents each of which is independently selected from $R^5$, and
(8) heteroaryl$C_{2-10}$alkenyl-, wherein heteroaryl is defined above and alkenyl is unsubstituted or substituted with one, two or three substituents each of which is independently selected from $R^5$;

X is selected from:
(1) a single bond,
(2) —O—, and
(3) —$NR^8$—;

n is an integer selected from 0 to 8;
and pharmaceutically acceptable salts thereof.

2. The method of claim 1 wherein the compound of Formula I:

$R^1$ is unsubstituted $C_{1-10}$alkyl;
$R^2$ is hydrogen;
$R^3$ is selected from:
(1) hydrogen,
(2) —$CH_2$-phenyl, and
(3) unsubstituted $C_{1-10}$alkyl;

$R^4$ is selected from:
(1) —NH—C(=O)-phenyl,
(2) —NH—C(=O)-naphthyl,
(3) —NH—C(=O)-(unsubstituted $C_{1-10}$alkyl)-phenyl, wherein the phenyl is unsubstituted or substituted with one or two substituents selected from: fluoro, chloro, and trifluoromethyl,
(4) —NH—C(=O)-(unsubstituted $C_{1-10}$alkyl),
(5) —C(=O)—NH-(unsubstituted $C_{1-10}$alkyl), and
(6) —C(=O)—NH—$CH_2$-phenyl;

and pharmaceutically acceptable salts thereof.

3. The method of claim 1 wherein the compound of Formula I:

heteroaryl is quinolinyl, substituted with —$NH_2$ and with —$CH_3$.

4. The method of claim 1 wherein the compound is of Formula Ia:

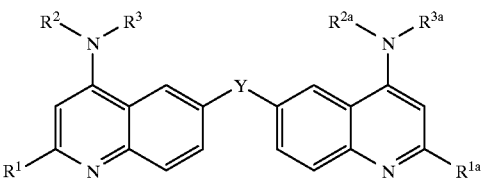

Ia wherein:
$R^1$ and $R^{1a}$ are independently selected from:
(1) hydrogen,
(2) $C_{1-10}$alkyl, which is unsubstituted or substituted with one, two or three substituents each of which is independently selected from $R^5$,
(3) aryl, wherein aryl is selected from: phenyl and naphthyl which is unsubstituted or substituted with one, two or three substituents each of which is independently selected from $R^5$, and
(4) aryl$C_{1-10}$alkyl-, wherein aryl is defined above and alkyl is unsubstituted or substituted with one, two or three substituents each of which is independently selected from $R^5$;
$R^2$, $R^{2a}$, $R^3$ and $R^{3a}$ are independently selected from:
(1) hydrogen,
(2) $C_{1-10}$alkyl, which is unsubstituted or substituted with one, two or three substituents each of which is independently selected from $R^5$,
(3) aryl, wherein aryl is defined above,
(4) aryl$C_{1-10}$alkyl-, wherein aryl is defined above and alkyl is unsubstituted or substituted with one, two or three substituents each of which is independently selected from $R^5$,
or $R^2$ and $R^3$ or $R^{2a}$ and $R^{3a}$ together with the nitrogen to which they are attached form a heterocyclic ring of 5 to 7 members selected from pyrrolidine, piperidine, piperazine, morpholine and thiomorpholine, wherein the heterocyclic ring optionally contains an additional group selected from —O—, —S—, and —NR$^{6a}$—, wherein $R^{6a}$ is independently selected from:
(a) hydrogen,
(b) phenyl, and
(c) $C_{1-10}$alkyl;
and wherein the heterocyclic ring is unsubstituted or substituted with one, two or three substituents each of which is independently selected from $R^5$;
Y is selected from:
(1) —NH$^8$—C(=O)—NR$^8$—, wherein $R^8$ and $R^9$ are independently selected from:
(a) hydrogen,
(b) phenyl, and
(c) $C_{1-10}$alkyl;
(2) —NH$^8$—C(=O)—(CH$_2$)$_n$—C(=O)—NR$^8$—;
(3) —NH$^8$—S(=O)$_2$—NR$^8$—, and
(4) —C(=O)—NH—;
$R^5$ is selected from:
(1) —O—R$^8$,
(2) —NO$_2$,
(3) halogen, wherein halogen is fluoro, chloro, bromo, or iodo,
(4) —S(=O)$_2$—R$^8$,
(5) —S—R$^8$,
(6) —S(=O)$_2$—NR$^8$R$^9$,
(7) —$C_{1-10}$alkyl,
(8) —NR$^8$R$^9$,
(9) —C(=O)—OR$^8$,
(10) —X—C(=O)—R$^8$,
(11) —CN,
(12) —C(=O)—NR$^8$R$^9$,
(13) —X—C(=O)—R$^8$,
(14) —NR$^{10}$—C(=O)—NR$^8$R$^9$, wherein $R^{10}$ is selected from:
(a) hydrogen,
(b) phenyl, and
(c) $C_{1-10}$alkyl;
(15) —NR$^{10}$—S(=O)$_2$—R$^8$,
(16) —NR$^{10}$—C(=NR$_2$)—NR$^8$R$^9$,
(17) —C(=NR$^{10}$)—NR$^8$R$^9$, and
(18) —CF$_3$;
n is an integer selected from 0 to 8;
and pharmaceutically acceptable salts thereof.

5. The method of claim 4 wherein the compound of Formula Ia:
$R^1$ and $R^{1a}$ are unsubstituted $C_{1-10}$alkyl;
$R^2$ and $R^{2a}$ are hydrogen;
$R^3$ and $R^{3a}$ are independently selected from:
(1) hydrogen,
(2) —CH$_2$-phenyl, and
(3) unsubstituted $C_{1-10}$alkyl;
Y is selected from:
(1) —NH—C(=O)—NH—,
(2) —NH—C(=O)—C(=O)—NH—,
(3) —NH—C(=O)—CH$_2$—C(=O)—NH—,
(4) —NH—C(=O)—(CH$_2$)$_4$—C(=O)—NH—,
(5) —NH—C(=O)—(CH$_2$)$_6$—C(=O)—NH—, and
(6) —NH—C(=O)—(CH$_2$)$_8$—C(=O)—NH—;
and pharmaceutically acceptable salts thereof.

6. The method of claim 1 wherein the compound is selected from the group consisting of:
4,6-Diamino-2-methyl-quinoline;
4-Amino-6-(2'-chloro-trans-cinnamoyl)amino-2-methyl-quinoline;
4-Amino-6-(trans-cinnamoyl)amino-2-methyl-quinoline;
4-Amino-6-(2-phenylethyl)amino-2-methyl-quinoline;
4-Amino-6-(2',6'-dichloro-trans-cinnamoyl)amino-2-methyl-quinoline;
4-Amino-6-(benzoyl)amino-2-methyl-quinoline;
4-Amino-6-(2'-naphthoyl)amino-2-methyl-quinoline;
4-Amino-6-(butanoyl)amino-2-methyl-quinoline;
4-Amino-6-(octanoyl)amino-2-methyl-quinoline;
4-Amino-6-(octadecanoyl)amino-2-methyl-quinoline;
4-Amino-6-(2'-trifluoromethyl-trans-cinnamoyl)amino-2-methyl-quinoline;
4-Amino-6-(3'-trifluoromethyl-trans-cinnamoyl)amino-2-methyl-quinoline;
4-Amino-6-(4'-trifluoromethyl-trans-cinnamoyl)amino-2-methyl-quinoline;
6-(2'-Chloro-trans-cinnamoyl)amino-4-methoxy-2-methyl-quinoline;
6-Amino-4-benzylamino-2-methyl-quinoline;
4-Benzylamino-6-(2'-chloro-trans-cinnamoyl)amino-2-methyl-quinoline;
4-Benzylamino-6-(2'-trifluoro-trans-cinnamoyl)amino-2methyl-quinoline;
4-n-Octylamino-6-(2'-chloro-trans-cinnamoyl)amino-2-methyl-quinoline;
4-Amino-2-methyl-quinoline, N-n-octyl-6-carboxamide;
4-Amino-2-methyl-quinoline, N-benzyl-6-carboxamide;
N,N'-Bis(4-amino-2-methyl-6-quinolyl)urea;
N,N'-Bis(4-amino-2-methyl-6-quinolyl)oxalamide;
N,N'-Bis(4-amino-2-methyl-6-quinolyl)malonamide;
N,N'-Bis(4-amino-2-methyl-6-quinolyl)adipamide;

N,N'-Bis(4-amino-2-methyl-6-quinolyl)sebacamide;
N,N'-Bis(4-benzylamino-2-methyl-6-quinolyl)oxalamide;
N,N'-Bis(2-methyl-6-quinolyl)urea;
and pharmaceutically acceptable salts thereof.

7. A method for preventing infection by HIV, treating infection by HIV, delaying of the onset of AIDS, or treating AIDS comprising the administration to a patient of an effective amount of a compound of formula I:

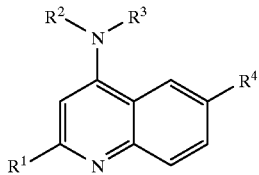

I wherein
$R^1$ is selected from:
(1) hydrogen,
(2) $C_{1-10}$alkyl, which is unsubstituted or substituted with one, two or three substituents each of which is independently selected from $R^5$,
(3) aryl, wherein aryl is selected from: phenyl and naphthyl which is unsubstituted or substituted with one, two or three substituents each of which is independently selected from $R^5$,
(4) aryl$C_{1-10}$alkyl-, wherein aryl is defined above and alkyl is unsubstituted or substituted with one, two or three substituents each of which is independently selected from $R^5$,
(5) heteroaryl, wherein heteroaryl is selected from: benzimidazolyl, benzofuranyl, benzooxazolyl, furanyl, imidazolyl, indolyl, isooxazolyl, isoquinolinyl, isothiazolyl, oxadiazolyl, oxazolyl, pyrazinyl, pyrazolyl, pyridyl, pyrimidyl, pyrrolyl, quinolinyl, tetrazolyl, thiadiazolyl, thiazolyl, thienyl, triazolyl, which is unsubstituted or substituted with one, two or three substituents each of which is independently selected from $R^5$, and
(6) heteroaryl$C_{1-10}$alkyl-, wherein heteroaryl is defined above and alkyl is unsubstituted or substituted with one, two or three substituents each of which is independently selected from $R^5$;

$R^2$ and $R^3$ are independently selected from:
(1) hydrogen,
(2) $C_{1-10}$alkyl, which is unsubstituted or substituted with one, two or three substituents each of which is independently selected from $R^5$,
(3) aryl, wherein aryl is defined above,
(4) aryl$C_{1-10}$alkyl-, wherein aryl is defined above and alkyl is unsubstituted or substituted with one, two or three substituents each of which is independently selected from $R^5$, or $R^2$ and $R^3$ together with the nitrogen to which they are attached form a heterocyclic ring of 5 to 7 members, selected from pyrrolidine, piperidine, piperazine, morpholine and thiomorpholine, wherein the heterocyclic ring optionally contains an additional group selected from —O—, —S—, and —NR$^6$—, and wherein the heterocyclic ring is unsubstituted or substituted with one, two or three substituents each of which is independently selected from $R^5$;

$R^4$ is selected from:
(1) —NH—C(=O)—X—R$^7$,
(2) —C(=O)—NH—R$^7$,
(3) —NH—C(=O)—(CH$_2$)$_n$—C(=O)—NH—R$^7$,
(4) —NH—S(=O)$_2$—X—R$^7$, and
(5) —NR$^8$R$^9$, wherein R$^8$ and R$^9$ are independently selected from:
(a) hydrogen,
(b) phenyl, and
(c) $C_{1-10}$alkyl;

$R^5$ is selected from:
(1) —O—R$^8$,
(2) —NO$_2$,
(3) halogen, wherein halogen is fluoro, chloro, bromo, or iodo,
(4) —S(=O)$_2$—R$^8$,
(5) —S—R$^8$,
(6) —S(=O)$_2$—NR$^8$R$^9$,
(7) —C$_{1-10}$alkyl,
(8) —NR$^8$R$^9$,
(9) —C(=O)—OR$^8$,
(10) —X—C(=O)—R$^8$,
(11) —CN,
(12) —C(=O)—NR$^8$R$^9$,
(13) —X—C(=O)—R$^8$,
(14) —NR$^{10}$—C(=O)—NR$^8$R$^9$, wherein R$^{10}$ is selected from:
(a) hydrogen,
(b) phenyl, and
(c) $C_{1-10}$alkyl;
(15) —NR$^{10}$—S(=O)$_2$—R$^8$,
(16) —NR$^{10}$—C(=NR$^{11}$)—NR$^8$R$^9$, wherein R$^{11}$ is selected from:
(a) hydrogen,
(b) phenyl, and
(c) $C_{1-10}$alkyl;
(17) —C(=NR$^{10}$)—NR$^8$R$^9$, and
(18) —CF$_3$;

$R^6$ is selected from:
(1) hydrogen,
(2) $C_{1-10}$alkyl, which is unsubstituted or substituted with one, two or three substituents each of which is independently selected from $R^5$,
(3) aryl, wherein aryl is defined above,
(4) aryl$C_{1-10}$alkyl-, wherein aryl is as defined above and alkyl is unsubstituted or substituted with one, two or three substituents each of which is independently selected from $R^5$,
(5) —C(=O)—X—C$_{1-10}$alkyl, wherein alkyl is unsubstituted or substituted with one, two or three substituents each of which is independently selected from $R^5$,
(6) —S(=O)$_2$—X—C$_{1-10}$alkyl, wherein alkyl is unsubstituted or substituted with one, two or three substituents each of which is independently selected from $R^5$,
(7) —C(=O)—X—aryl, wherein aryl is defined above, and
(8) —S(=O)$_2$—X—aryl, wherein aryl is defined above;

$R_7$ is selected from:
(1) hydrogen,
(2) $C_{1-10}$alkyl, which is unsubstituted or substituted with one, two or three substituents each of which is independently selected from $R^5$,
(3) aryl, wherein aryl is defined above,
(4) aryl$C_{1-10}$alkyl-, wherein aryl is defined above and alkyl is unsubstituted or substituted with one, two or three substituents each of which is independently selected from $R^5$, (5) arylC$_{2-10}$alkenyl-, wherein aryl is defined above and alkenyl is unsubstituted or substituted with one, two or three substituents each of which is independently selected from R$^5$,
(6) heteroaryl, wherein heteroaryl is defined above, and
(7) heteroarylC$_{1-10}$alkyl-, wherein heteroaryl is defined above and alkyl is unsubstituted or substituted with one, two or three substituents each of which is independently selected from R$^5$, and
(8) heteroarylC$_{2-10}$alkenyl-, wherein heteroaryl is defined above and alkenyl is unsubstituted or substituted with one, two or three substituents each of which is independently selected from R$^5$;

X is selected from:
(1) a single bond,
(2) —O—, and
(3) —NR$^8$—;

n is an integer selected from 0 to 8;
and pharmaceutically acceptable salts thereof.

8. The method of claim 7 wherein the compound of Formula I:
R$^1$ is unsubstituted C$_{1-10}$alkyl;
R$^2$ is hydrogen;
R$^3$ is selected from:
(1) hydrogen,
(2) —CH$_2$-phenyl, and
(3) unsubstituted C$_{1-10}$alkyl;
R$^4$ is selected from:
(1) —NH—C(=O)-phenyl,
(2) —NH—C(=O)-naphthyl,
(3) —NH—C(=O)-(unsubstituted C$_{1-10}$alkyl)-phenyl, wherein the phenyl is unsubstituted or substituted with one or two substituents selected from: fluoro, chloro, and trifluoromethyl,
(4) —NH—C(=O)-(unsubstituted C$_{1-10}$alkyl),
(5) —C(=O)—NH-(unsubstituted C$_{1-10}$alkyl), and
(6) —C(=O)—NH—CH$_2$-phenyl;
and pharmaceutically acceptable salts thereof.

9. The method of claim 7 wherein the compound of Formula I:
heteroaryl is quinolinyl, substituted with —NH$_2$ and with —CH$_3$.

10. The method of claim 7 wherein the compound is of Formula Ia:

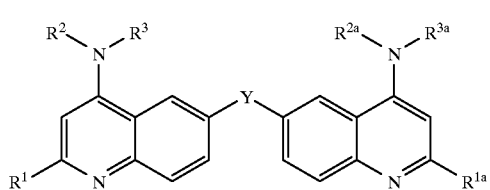

Ia wherein:
R$^1$ and R$_{1a}$ are independently selected from:
(1) hydrogen,
(2) C$_{1-10}$alkyl, which is unsubstituted or substituted with one, two or three substituents each of which is independently selected from R$^5$,
(3) aryl, wherein aryl is selected from: phenyl and naphthyl which is unsubstituted or substituted with one, two or three substituents each of which is independently selected from R$^5$, and
(4) arylC$_{1-10}$alkyl-, wherein aryl is defined above and alkyl is unsubstituted or substituted with one, two or three substituents each of which is independently selected from R$^5$;

R$^2$, R$^{2a}$, R$^3$ and R$^{3a}$ are independently selected from:
(1) hydrogen,
(2) C$_{1-10}$alkyl, which is unsubstituted or substituted with one, two or three substituents each of which is independently selected from R$^5$,
(3) aryl, wherein aryl is defined above,
(4) arylC$_{1-10}$alkyl-, wherein aryl is defined above and alkyl is unsubstituted or substituted with one, two or three substituents each of which is independently selected from R$^5$, or R$^2$ and R$^3$ or R$^{2a}$ and R$^{3a}$ together with the nitrogen to which they are attached form a heterocyclic ring of 5 to 7 members, selected from pyrrolidine, piperidine, piperazine, morpholine and thiomorpholine, wherein the heterocyclic ring optionally contains an additional group selected from —O—, —S—, and —NR$^{6a}$—, wherein R$^{6a}$ is independently selected from:
(a) hydrogen,
(b) phenyl, and
(c) C$_{1-10}$alkyl;
and wherein the heterocyclic ring is unsubstituted or substituted with one, two or three substituents each of which is independently selected from R$^5$;

Y is selected from:
(1) —NH$^8$—C(=O)—NR$^8$—, wherein R$^8$ and R$^9$ are independently selected from:
(a) hydrogen,
(b) phenyl, and
(c) C$_{1-10}$alkyl;
(2) —NH$^8$—C(=O)—(CH$_2$)$_n$—C(=O)—NR$^8$—;
(3) —NH$^8$—S(=O)$_2$—NR$^8$—, and
(4) —C(=O)—NH—;

R$^5$ is selected from:
(1) —O—R$^8$,
(2) —NO$_2$,
(3) halogen, wherein halogen is fluoro, chloro, bromo, or iodo,
(4) —S(=O)$_2$—R$^8$,
(5) —S—R$^8$,
(6) —S(=O)$_2$—NR$^8$R$^9$,
(7) —C$_{1-10}$alkyl,
(8) —NR$^8$R$^9$,
(9) —C(=O)—OR$^8$,
(10) —X—C(=O)—R$^8$,
(11) —CN,
(12) —C(=O)—NR$^8$R$^9$,
(13) —X—C(=O)—R$^8$,
(14) —NR$^{10}$—C(=O)—NR$^8$R$^9$, wherein R$^{10}$ is selected from:
(a) hydrogen,
(b) phenyl, and
(c) C$_{1-10}$alkyl;
(15) —NR$^{10}$—S(=O)$_2$—R$^8$,
(16) —NR$^{10}$—C(=NR$_2$)—NR$^8$R$^9$,
(17) —C(=NR$^{10}$)—NR$^8$R$^9$, and
(18) —CF$_3$;

n is an integer selected from 0 to 8;
and pharmaceutically acceptable salts thereof.

11. The method of claim 10 wherein the compound of Formula Ia:
R$^1$ and R$^{1a}$ are unsubstituted C$_{1-10}$alkyl;
R$^2$ and R$^{2a}$ are hydrogen;
R$^3$ and R$^{3a}$ are independently selected from:
(1) hydrogen, (2) —CH₂-phenyl, and
(3) unsubstituted $C_{1-10}$alkyl;
Y is selected from:
(1) —NH—C(=O)—NH—,
(2) —NH—C(=O)—C(=O)—NH—,
(3) —NH—C(=O)—CH₂—C(=O)—NH—,
(4) —NH—C(=O)—(CH₂)₄—C(=O)—NH—,
(5) —NH—C(=O)—(CH₂)₆—C(=O)—NH—, and
(6) —NH—C(=O)—(CH₂)₈—C(=O)—NH—;
and pharmaceutically acceptable salts thereof.

12. The method of claim 7 wherein the compound is selected from the group consisting of:
4,6-Diamino-2-methyl-quinoline;
4-Amino-6-(2'-chloro-trans-cinnamoyl)amino-2-methyl-quinoline;
4-Amino-6-(trans-cinnamoyl)amino-2-methyl-quinoline;
4-Amino-6-(2-phenylethyl)amino-2-methyl-quinoline;
4-Amino-6-(2',6'-dichloro-trans-cinnamoyl)amino-2-methyl-quinoline;
4-Amino-6-(benzoyl)amino-2-methyl-quinoline;
4-Amino-6-(2'-naphthoyl)amino-2-methyl-quinoline;
4-Amino-6-(butanoyl)amino-2-methyl-quinoline;
4-Amino-6-(octanoyl)amino-2-methyl-quinoline;
4-Amino-6-(octadecanoyl)amino-2-methyl-quinoline;
4-Amino-6-(2'-trifluoromethyl-trans-cinnamoyl)amino-2methyl-quinoline;
4-Amino-6-(3'-trifluoromethyl-trans-cinnamoyl)amino-2-methyl-quinoline;
4-Amino-6-(4'-trifluoromethyl-trans-cinnamoyl)amino-2-methyl-quinoline;
6-(2'-Chloro-trans-cinnamoyl)amino-4-methoxy-2-methyl-quinoline;
6-Amino-4-benzylamino-2-methyl-quinoline;
4-Benzylamino-6-(2'-chloro-trans-cinnamoyl)amino-2-methyl-quinoline;
4-Benzylamino-6-(2'-trifluoro-trans-cinnamoyl)amino-2-methyl-quinoline;
4-n-Octylamino-6-(2'-chloro-trans-cinnamoyl)amino-2-methyl-quinoline;
4-Amino-2-methyl-quinoline, N-n-octyl-6-carboxamide;
4-Amino-2-methyl-quinoline, N-benzyl-6-carboxamide;
N,N'-Bis(4-amino-2-methyl-6-quinolyl)urea;
N,N'-Bis(4-amino-2-methyl-6-quinolyl)oxalamide;
N,N'-Bis(4-amino-2-methyl-6-quinolyl)malonamide;
N,N'-Bis(4-amino-2-methyl-6-quinolyl)adipamide;
N,N'-Bis(4-amino-2-methyl-6-quinolyl)sebacamide;
N,N'-Bis(4-benzylamino-2-methyl-6-quinolyl)oxalamide;
N,N'-Bis(2-methyl-6-quinolyl)urea;
and pharmaceutically acceptable salts thereof.

* * * * *